(12) United States Patent
Herzig et al.

(10) Patent No.: US 6,878,770 B2
(45) Date of Patent: Apr. 12, 2005

(54) AQUEOUS ORGANOSILICON COMPOSITIONS

(75) Inventors: Christian Herzig, Waging am See (DE); Wolfgang Schattenmann, Burghausen (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/333,938

(22) PCT Filed: Mar. 22, 2001

(86) PCT No.: PCT/EP01/03291

§ 371 (c)(1),
(2), (4) Date: Jul. 30, 2003

(87) PCT Pub. No.: WO02/10254

PCT Pub. Date: Feb. 7, 2002

(65) Prior Publication Data

US 2004/0029981 A1 Feb. 12, 2004

(30) Foreign Application Priority Data

Jul. 27, 2000 (DE) .......................... 100 36 677

(51) Int. Cl.⁷ .............................................. C08G 77/26
(52) U.S. Cl. ................. 524/588; 524/838; 106/287.11; 528/28
(58) Field of Search ........................... 524/588; 528/28; 106/298.11

(56) References Cited

U.S. PATENT DOCUMENTS

| 2,971,864 A | | 2/1961 | Speier et al. |
| 3,389,160 A | | 6/1968 | Wallace et al. |
| 4,101,272 A | | 7/1978 | Guise et al. |
| 4,833,225 A | | 5/1989 | Schaefer et al. |
| 5,707,434 A | * | 1/1998 | Halloran et al. ....... 106/287.11 |
| 5,807,956 A | | 9/1998 | Czech |
| 6,001,422 A | | 12/1999 | Hirai et al. |
| 6,240,929 B1 | * | 6/2001 | Richard et al. ............. 132/202 |

OTHER PUBLICATIONS

J.L. Speier et al., J. Org. Chem 36, p. 3120 (1971).

* cited by examiner

*Primary Examiner*—Margaret G. Moore
(74) *Attorney, Agent, or Firm*—Brooks Kushman P.C.

(57) ABSTRACT

The invention relates to novel aqueous compositions containing (1) organosilicon compounds comprising ammonium groups, containing at least one grouping consisting of two protonated nitrogen atoms per molecule, said atoms being linked by at least three carbon atoms, (2) acid anions, the corresponding acids thereof having a $pk_a$ value higher than 0, (3) water, (4) optionally a solvent which can be mixed with water, and (5) optionally emulsifying agents. Said aqueous compositions are preferably homogeneous aqueous solutions.

6 Claims, No Drawings

AQUEOUS ORGANOSILICON COMPOSITIONS

BACKGROUND OF THE INVENTION

1. Field of the Invention

This invention relates to aqueous compositions comprising organosilicon compounds.

2. Description of the Related Art

U.S. Pat. No. 4,101,272 (Commonwealth Scientific and Industrial Research Organization, issued Jul. 18, 1978) describes a process for the treatment of wool that comprises epoxysiloxanes and amines being applied to the wool as separate substances and reacting in situ to form crosslinked insoluble structures.

U.S. Pat. No. 4,833,225 (Goldschmidt, issued May 23, 1989) discloses polyquaternary polysiloxane polymers of the block structure $(AB)_n A$, which are obtained by reaction of $\alpha,\omega$-epoxysiloxanes with ditertiary diamines in the presence of acids. The block copolymers contain quaternary nitrogen atoms.

U.S. Pat. No. 5,807,956 (OSi Specialties, Inc., issued Sep. 15, 1998) describes block copolymers of the structure $(AB)_n A$ which contain polyalkylene oxide chains. They are prepared by reacting $\alpha,\omega$-epoxysiloxanes with $\alpha,\omega$-aminoalkyl polyethers, although the poor mutual solubility of the reactants means that relatively large amounts of organic solvents are needed to achieve adequate compatibility.

U.S. Pat. No. 6,001,422 (Shin-Etsu Chemical Co., issued Dec. 14, 1999) discloses aminoalkyl-containing diorganopolysiloxanes and their use in aqueous formulations whose basic nitrogen atoms are separated by —$CH_2$—$CH_2$-groups. The aminosiloxanes described have amine equivalent values from 5 000 to 100 000 g/mol, corresponding to an amine nitrogen content from 0.014 to 0.28% by weight.

SUMMARY OF THE INVENTION

It is an object of the present invention to provide aqueous compositions of organosilicon compounds which contain organic radicals containing basic nitrogen which, in particular, are soluble or self-dispersing in water and most preferably have a lower basic nitrogen content than hitherto. These and other objects are achieved by the invention, wherein the organosilicon compounds are dispersed in water, and are ammonium group-containing ("ammonio-containing") organosilicon compounds containing at least one moiety containing two protonated nitrogen atoms joined together by a hydrocarbon radical of at least three carbon atoms, and acid anions derived from an acid having a $pk_a$ greater than zero.

DETAILED DESCRIPTION OF THE INVENTION

The present invention accordingly provides aqueous compositions containing (1) ammonio-containing organosilicon compounds which, per molecule, contain at least one moiety of two protonated nitrogen atoms joined together through at least three carbon atoms, (2) acid anions whose corresponding acids have a $pk_a$ value of greater than 0, preferably greater than 2 and more preferably greater than 3, (3) water, optionally (4) water-miscible solvents and optionally (5) emulsifiers.

The aqueous compositions are preferably homogeneous aqueous solutions, aqueous microemulsions and aqueous emulsions, of which homogeneous aqueous solutions are preferred.

The aqueous compositions according to the present invention are prepared by mixing the inventive (1) ammonio-containing organosilicon compounds together with their (2) acid anions with (3) water, optionally (4) water-miscible solvents and optionally (5) emulsifiers.

The inventive (1) ammonio-containing organosilicon compounds together with their (2) acid anions are preferably obtained by reacting the amino-containing organosilicon compounds corresponding to (1) with acids corresponding to (2).

The use of (5) emulsifiers is not preferred.

The inventive (1) ammonio-containing organosilicon compounds preferably contain at least one moiety of the general formula

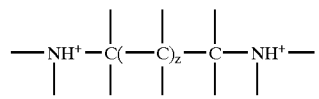

where z is an integer from 1 to 20.

Preferred inventive ammonio-containing organosilicon compounds contain
(a) at least one structural unit Y of the general formula

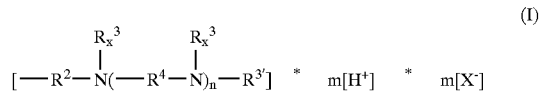

(I)

where $R^2$ is a divalent organic radical, $R^3$ is a hydrogen atom or a monovalent hydrocarbon radical having 1 to 60 carbon atoms per radical which may be interrupted or substituted by one or more separate hetero atoms selected from the group consisting of nitrogen, oxygen, sulfur and halogen, $R^{3'}$ has the meaning of $R^3$, preferably a hydrogen atom or a monovalent hydrocarbon radical having 1 to 12 carbon atoms per radical, $R^4$ is a divalent hydrocarbon radical having 1 to 10 carbon atoms per radical, preferably 3 to 10 carbon atoms per radical, n is 0 or an integer from 1 to 10, m is an integer from 1 to the total number of nitrogen atoms in (I), preferably an integer from 2 to the sum formed from n+1 and the total number of any basic nitrogen atoms contained in the $R^3$ radicals, and each x is the same or different and represents 1, $X^-$ is an acid anion whose corresponding acid has a $pK_a$ value greater than 0, preferably greater than 2, more preferably greater than 3, with the proviso that the structural unit of formula (I) contains at least one moiety of two protonated nitrogen atoms which are joined together through at least three carbon atoms, and (b) at least one siloxane unit of the general formula

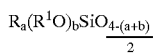   (II)

where each R is the same or different and represents a monovalent optionally halogenated hydrocarbon radical having 1 to 18 carbon atoms per radical, each $R^1$ is the same or different and represents a monovalent hydrocarbon radical having 1 to 8 carbon atoms per radical, a is 0, 1, 2 or 3, b is 0, 1, 2 or 3, with the proviso that the sum of a+b is $\leq 3$, and (c) at least one siloxane unit of the general formula

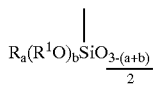   (III)

where R, $R^1$, a and b are each as defined above, with the proviso that the sum of a+b is $\leq 2$ and that the siloxane unit of the formula (III) is bonded through the silicon atoms to the structural unit of the formula (I) through the $R^2$ radicals, and optionally (d) at least one structural unit Y' of the general formula

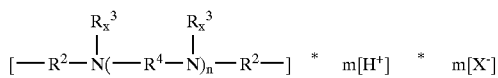   (I')

where $R^2$, $R^3$, $R^4$, n, m x and $X^-$ are each as defined above, with the proviso that the structural unit of the formula (I') contains at least one moiety of two protonated nitrogen atoms which are joined together through at least three carbon atoms, and (e) at least two siloxane units of the general formula

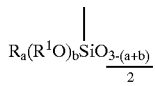   (III')

where R, $R^1$, a and b are each as defined above, with the proviso that the sum of a+b is $\leq 2$ and that the siloxane units of the formula (III') are joined through the silicon atoms to the structural unit of the formula (I') through the $R^2$ radicals.

Preferred inventive ammonio-containing organosilicon compounds contain (a') at least one siloxane unit of the general formula

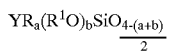   (IV)

where Y is an organic radical of formula (I) and
R, $R^1$, a and b are each as defined above, with the proviso that the sum of a+b is $\leq 2$, (b) at least one siloxane unit of the general formula

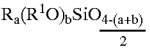   (II)

where R, $R^1$, a and b are each as defined above, with the proviso that the sum of a+b is $\leq 3$, and optionally (d') at least one bridge unit of the general formula

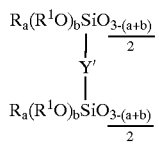   (V)

where Y' is an organic radical of the formula (I') and
R, $R^1$, a and b are each as defined above, with the proviso that the sum of a+b is $\leq 2$.

The ammonium nitrogen content is preferably from 0.3 to 5.0% by weight and more preferably from 0.5 to 5.0% by weight, each percentage being based on the total weight of the ammonio-containing organosilicon compounds.

The viscosity of the inventive ammonio-containing organosilicon compounds is preferably 50–5 000 000 mPa·s at 25° C. and more preferably 100–100 000 mPa·s at 25° C.

The inventive ammonio-containing organosilicon compounds are preparable by reaction of (poly)amines with epoxy-containing organosilicon compounds.

When the (poly)amine contains just one nitrogen-attached hydrogen atom, a monoaddition takes place.

The monoaddition of (poly)amines having an N-attached hydrogen atom to epoxy-containing organosilicon compounds is known and described for example in U.S. Pat. No. 3,389,160 (Union Carbide Corporation).

When the (poly)amine contains at least two nitrogen-attached hydrogen atoms, a polyaddition takes place.

The nitrogen atoms are then protonated by reaction with acids.

When the inventive ammonio-containing organosilicon compounds are prepared by the abovementioned polyaddition, they will contain the units (d) and (e), ie the bridge units (d'), in addition to the units (a), (b) and (c) or (a') and (b) as the case may be.

Useful inventive ammonio-containing organosilicon compounds are further prepared by reaction of chloroalkylalkoxysilanes, such as chloroalkyldimethoxymethylsilanes, with (poly)amines, such as hexamethylenediamine, and equilibration of the resultant aminoalkylalkoxysilanes, such as aminoalkyldimethoxymethylsilanes, or their hydrolysis and/or condensation products, with organopolysiloxanes, such as linear triorganosiloxy-terminated organopolysiloxanes, linear hydroxyl-terminated organopolysiloxanes, cyclic organopolysiloxanes or copolymers of diorganosiloxane and monoorganosiloxane units.

The nitrogen atoms are then protonated by reaction with acids.

Such amino-functional organosilicon compounds and also their preparation are known and described for example in U.S. Pat. No. 2,971,864 (Dow Corning Corporation, issued Feb. 14, 1961) and J. L. Speier et al., J. ORG. CHEM. 36, 3120 (1971).

Examples of R radicals are alkyl radicals, such as methyl, ethyl, n-propyl, isopropyl, n-butyl, isobutyl, tert-butyl, n-pentyl, isopentyl, neopentyl, tert-pentyl, hexyl, such as n-hexyl, heptyl, such as n-heptyl, octyl, such as n-octyl and isooctyl, such as 2,2,4-trimethylpentyl, nonyl, such as n-nonyl, decyl, such as n-decyl, dodecyl, such as n-dodecyl, and octadecyl, such as n-octadecyl, cycloalkyl, such as cyclopentyl, cyclohexyl, cycloheptyl and methylcyclohexyl, aryl, such as phenyl, naphthyl, anthryl and phenanthryl, alkaryl, such as o-, m-, p-tolyl, xylyl and ethylphenyl, and aralkyl, such as benzyl, α-phenylethyl and β-phenylethyl.

Examples of substituted R radicals are haloalkyl, such as 3,3,3-trifluoro-n-propyl, 2,2,2,2',2',2'-hexafluoroisopropyl, heptafluoroisopropyl and haloaryl, such as o-, m- and p-chlorophenyl.

R is preferably methyl.

Examples of $R^1$ radicals are alkyl, such as methyl, ethyl, n-propyl, isopropyl, n-butyl, isobutyl, tert-butyl, n-pentyl, isopentyl, neopentyl, tert-pentyl, hexyl, such as n-hexyl, heptyl, such as n-heptyl, octyl, such as n-octyl and isooctyl, such as 2,2,4-trimethylpentyl.

$R^2$ is preferably an organic radical selected from the group

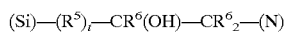  (VI),

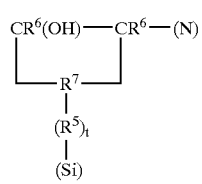  (VII)

and a divalent hydrocarbon radical having 1 to 10 carbon atoms per radical, where (Si)— is the bond to the silicon atom of the siloxane unit of the formula (IV) or (V) as the case may be and —(N) is the bond to the nitrogen atom of the structural unit Y or Y' of the formula (I) or (I') as the case may be, $R^5$ is a divalent hydrocarbon radical having 1 to 10 carbon atoms per molecule which may be substituted by an ether oxygen atom, $R^6$ is a hydrogen atom or a monovalent hydrocarbon radical having 1 to 10 carbon atoms per radical which may be substituted by an ether oxygen atom, $R^7$ is a trivalent hydrocarbon radical having 3 to 12 carbon atoms per radical and t is 0 or 1.

Examples of $R^2$ radicals are aliphatic, cycloaliphatic and aromatics-containing divalent organic radicals which contain hydroxyl functions from the epoxide ring opening such as

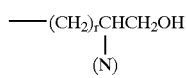

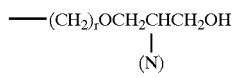

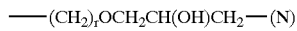

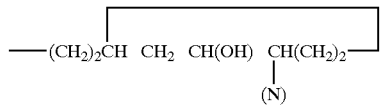

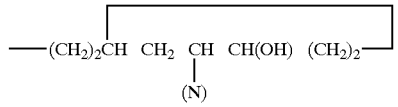

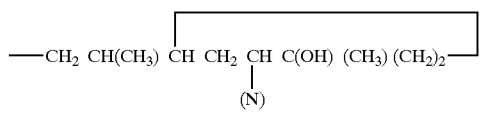

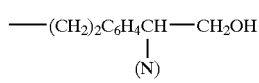

where r is an integer from 1 to 20 and preferably from 2 to 8, and —(N) is the bond to the nitrogen atom of the structural unit Y of the formula (I)

and alkylene radicals, such as

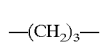

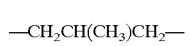

Preferred R² radicals are

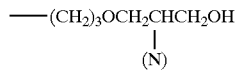

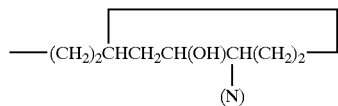

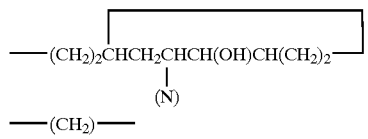

—CH₂CH(CH₃)CH₂—

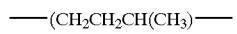

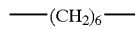

and the first two radicals and the —(CH₂)₃— radical are particularly preferred.

Examples of R³ hydrocarbon radicals are alkyl radicals, such as methyl, ethyl, n-propyl, isopropyl, n-butyl, isobutyl, tert-butyl, n-pentyl, isopentyl, neopentyl, tert-pentyl, hexyl, such as n-hexyl, heptyl, such as n-heptyl, octyl, such as n-octyl and isooctyl, such as 2,2,4-trimethylpentyl, nonyl, such as n-nonyl, decyl, such as n-decyl, dodecyl, such as n-dodecyl, and octadecyl, such as n-octadecyl, cycloalkyl, such as cyclopentyl, cyclohexyl, cycloheptyl and methylcyclohexyl, aryl, such as phenyl, naphthyl, anthryl and phenanthryl, alkaryl, such as o-, m-, p-tolyl, xylyl and ethylphenyl, and aralkyl, such as benzyl, α-phenylethyl and β-phenylethyl.

Examples of R³ halogenated radicals are haloalkyl, such as 3,3,3-trifluoro-n-propyl, 2,2,2,2',2',2'-hexafluoroisopropyl, heptafluoroisopropyl and haloaryl, such as o-, m- and p-chlorophenyl.

Examples of R³ radicals substituted by a nitrogen atom are as the case may be

—C₂H₄NEt₂ or —C₂H₄N⁺HEt₂*X⁻

—C₂H₄NMe₂ or —C₂H₄N⁺HMe₂*X⁻

—C₃H₆NMe₂ or —C₃H₆N⁺HMe₂*X⁻

—C₃H₆NEt₂ or —C₃H₆N⁺HEt₂*X⁻

—C₄H₈NMe₂ or —C₄H₈N⁺HMe₂*X⁻

—C₂H₄NMeC₂H₄NMe₂ or —C₂H₄N⁺HMeC₂H₄N⁺HMe₂*2X⁻

—C₃H₆NEtC₃H₆NEt₂ or —C₃H₆N⁺HEtC₃H₆N⁺HEt₂*2X⁻

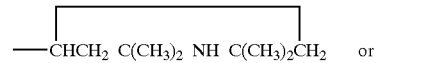

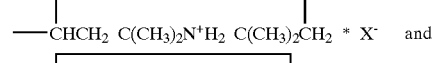

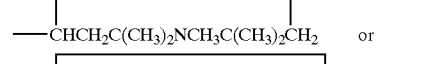

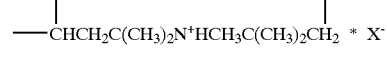

where Me is methyl and Et is ethyl.

Examples of R³ radicals substituted by an oxygen atom are

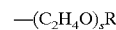

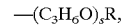

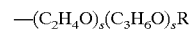

and

where s is an integer from 1 to 30, preferably from 1 to 20 and R is as defined above, preferably is methyl or butyl.

Examples of R³ radicals which are substituted by a nitrogen atom and an oxygen atom are as the case may be

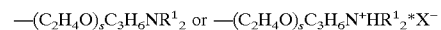

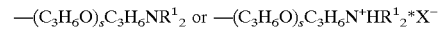

and

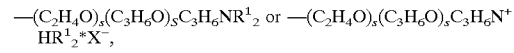

where s, R¹ and X⁻ are each as defined above and R¹ is preferably methyl or ethyl.

Examples of R³ radicals substituted by a sulfur atom are

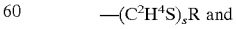

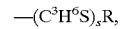

where s and R are each as defined above and R is preferably methyl, ethyl or butyl.

Examples of R⁴ radicals are

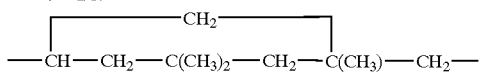

and radicals having at least three carbon atoms are preferred and the radicals

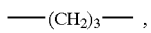

and

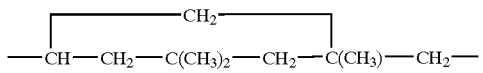

are particularly preferred.

n is preferably 0, 1, 2, 3, 4, 5, 6, 7, 8, 9 and 10.

The inventive ammonio-containing organosilicon compounds are preferably prepared by reaction of (poly)amines with epoxy-containing organosilicon compounds, especially by polyaddition.

The ammonio-containing organosilicon compounds obtained by polyaddition are preferably prepared by
in a first stage reacting
(poly)amines (11) of the general formula

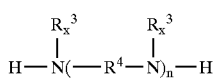

where $R^3$, $R^4$, n and x are each as defined above, with epoxy-containing organosilicon compounds (12) containing units of the general formula

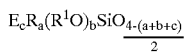

where R, $R^1$, a and b are each as defined above,
each E is the same or different and represents a monovalent SiC-attached organic radical which contains an epoxy group, and
c is 0 or 1,
with the proviso that the sum of a+b+c is ≦3 and that at least one E radical is present per molecule,
with the proviso that the employed ratio of N-attached hydrogen in (poly)amine (11) to epoxy group in organosilicon compound (12) is such that toluene-soluble amino-containing organosilicon compounds are obtained,
and in a second stage protonating
the amino-containing organosilicon compounds obtained in the first stage by addition of acids (14), preferably having a $pK_a$ value of greater than 0, more preferably of greater than 2 and most preferably of greater than 3, partially or fully and preferably fully,
with the proviso that the ammonio-containing organosilicon compounds obtained contain at least one moiety of two protonated nitrogen atoms joined together through at least three carbon atoms.

The amino-containing organosilicon compounds obtained in the first stage in the course of the polyaddition are soluble in toluene, ie are uncrosslinked, in contradistinction to toluene-insoluble organosilicon compounds which are crosslinked. The organosilicon compounds obtained are soluble in toluene in any proportion and are preferably 100 percent by weight soluble in toluene at a temperature of 25° C. and a pressure of about 1020 hPa on organosilicon compounds and toluene being mixed in a ratio of 1:1 (parts by weight) and preferably 1:10 (parts by weight).

The ammonio-containing organosilicon compounds obtained after the polyaddition contain siloxane blocks which are joined together through at least one di- or polyvalent ammonium radical.

Examples of (poly)amines (11) are primary amines of the general formula $R^3$—$NH_2$,
where $R^3$ is a radical which is substituted by a nitrogen atom, such as

4-amino-2,2,6,6-tetramethylpiperidine
and
4-amino-1,2,2,6,6-pentamethylpiperidine,
and primary amines of the general formula $R^3$—$NH_2$,
where $R^3$ is a radical substituted by an oxygen atom and a nitrogen atom, such as

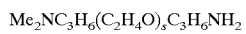

and

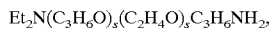

where s is as defined above,
Me is methyl, Et is ethyl and Bu is n-butyl.

Further examples of (poly)amines (11) are propylenediamine, 1,6-diaminohexane, dipropylenetriamine, isophoronediamine and neopentanediamine.

The E radicals preferably conform to the formula

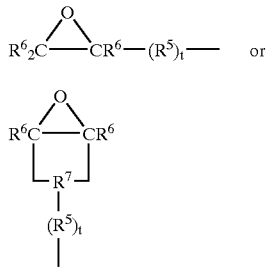

where $R^5$, $R^6$, $R^7$ and t are each as defined above.

The polyaddition is preferably carried out using epoxy-containing organosilicon compounds (12) conforming to the general formula $$E_dR_{3-d}SiO(SiR_2O)_o(SiREO)_pSiR_{3-d}E_d \qquad (VIII),$$

where R and E are each as defined above,
d is 0 or 1, and especially 1,
o is 0 or an integer from 1 to 1 000 and especially from 5 to 200, and
p is 0 or an integer from 1 to 10, preferably 0 or from 1 to 6 and more preferably 0.

The viscosity of the epoxy-containing organosilicon compounds (12) is preferably in the range from 1 to 100 000 mPa·s at 25° C. and more preferably in the range from 10 to 2 000 mPa·s at 25° C.

Examples of E radicals are
3,4-epoxybutyl,
5,6-epoxyhexyl,
7,8-epoxyoctyl,
glycidoxyethyl,
glycidoxypropyl,
2-(3,4-epoxycyclohexyl)ethyl,
2-(3-epoxyphenyl)ethyl
and also epoxy itself,
of which glycidoxypropyl and 2-(3,4-epoxycyclohexyl)ethyl are preferred and glycidoxypropyl is particularly preferred.

Processes for preparing epoxy-containing organosilicon compounds (12) are known to one skilled in the art.

Preferred embodiments are the epoxidation of aliphatically unsaturated organopolysiloxanes and the addition of terminally unsaturated organic epoxy compounds, such as allyl glycidyl ether or 4-vinylcyclohexene oxide, which is catalyzed by precious metal (compounds), to organopolysiloxanes containing silicon-attached hydrogen.

The epoxy-containing organosilicon compounds (12) used in the polyaddition preferably contain from 1 to 10 and especially from 1 to 6 epoxy groups per molecule. A particularly preferred embodiment is the use of α,ω-diepoxypolysiloxanes.

The polyaddition is preferably carried out using (poly)amines (11) containing from 2 to 10 nitrogen-attached hydrogen atoms and especially containing from 2 to 6 nitrogen-attached hydrogen atoms. The number of nitrogen atoms per molecule is initially not dependent thereon but is preferably in the range from 2 to 4.

The polyaddition may optionally employ amines (13) having just one N—H group per molecule, since these act as chain stoppers and thus render the polyaddition controllable.

Any amines (13) used preferably conform to the general formula

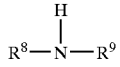

(IX)

where $R^8$ and $R^9$ are the same or different and each represent a monovalent hydrocarbon radical having 1 to 60 carbon atoms per radical which may be interrupted by one or more separate hetero atoms selected from the group consisting of nitrogen and oxygen, or
$R^8$ and $R^9$ together represent a divalent hydrocarbon radical having 4 to 10 carbon atoms.

Examples of amines (13) are dibutylamine, piperidine, diethanolamine, trimethylethylenediamine, bis(2-diethylaminoethyl)amine and bis(3-dimethylaminopropyl)amine.

Amines (13), when used, are preferably used in amounts from 5 to 40% by weight, based on the total weight of the (poly)amines (11).

In the polyaddition, the ratio of (poly)amines (11) to epoxy-containing organosilicon compounds (12) is preferably in the range from 1:1 to 10:1, more preferably in the range from 1:1 to 5:1 and most preferably in the range from 1:1 to 4:1.

In the polyaddition, the stoichiometry of the reaction depends on the ratio of nitrogen-attached hydrogen in (11) to epoxy groups in (12) (N—H/epoxy). This N—H/epoxy ratio can be varied within wide limits, according to the nature of the ingredients and the target range for the viscosities of the inventive organosilicon compounds. But preferably the N—H/epoxy ratio is not less than ≧1 in order that all the epoxy groups can react, subject to the condition that toluene-soluble, ie uncrosslinked, products are obtained. A person of ordinary skill in the art knows how to vary the N—H/epoxy ratio in the process of the present invention as a function of the N—H groups in (11) and epoxy groups in (12), i.e. the functionality of the reagents, for example experimentally by carrying out tests, so that toluene-soluble products may be obtained. Since secondary reactions and also incomplete reaction sequences with conversions below 100% of theory play a part, a person of ordinary skill in the art knows that possible limits must be determined experimentally if particularly viscous products are to be prepared.

The polyaddition is preferably carried out in the first stage at temperatures above 25° C., although there is detectable reaction even at the normal, ambient temperature.

But temperatures above 60° C. are preferable, temperatures in the range from 80 to 180° C. are more preferable and temperatures between 100 and 150° C. are most preferable in the interests of a rapid and complete reaction. The polyaddition is preferably carried out at the pressure of the ambient atmosphere, i.e. at about 1000 hPa, although particularly in the case of volatile (poly)amines (11) an elevated pressure is advantageous in order that losses of N—H functions through evaporation and hence a change in the stoichiometry may be avoided.

The $pK_a$ value of acids used in the preparation of the inventive ammonio-containing organosilicon compounds is preferably greater than 0, more preferably greater than 2 and most preferably greater than 3. Any kind of acid or various kinds of acid can be used. It is preferable to use water-soluble organic or inorganic acids.

Examples of acids are
monocarboxylic acids of the general formula R'—COOH (Xa) where R' is a hydrogen atom or a hydrocarbon radical having 1 to 18 carbon atoms per radical, such as formic acid, acetic acid, propionic acid, butyric acid, pivalic acid, sorbic acid, benzoic acid, salicylic acid and toluylic acid, and dicarboxylic acids of the general formula HOOC—R⁵—COOH (Xb), where $R^5$ is as defined above, such as succinic acid, maleic acid, adipic acid, malonic acid and phthalic acid, and the monocarboxylic acids are preferred.

Particular preference is given to formic acid, acetic acid and propionic acid.

Further examples of acids are sulfonic acids of the general formula

R'—SO₃H (Xc)

where R' is as defined above, such as methanesulfonic acid, butanesulfonic acid, trifluoromethanesulfonic acid and toluenesulfonic acid, and also inorganic acids, such as hydrochloric acid, hydrobromic acid, sulfuric acid and phosphoric acid. The exclusive use of these strong acids is not preferable.

Examples of R' hydrocarbon radicals are the hydrocarbon radicals R.

Accordingly, the organosilicon compounds according to the present invention preferably contain the corresponding $X^-$ anions of the acids used. Preferably, $X^-$ is an anion of a corresponding water-soluble organic or inorganic acid. Examples of $X^-$ anions are therefore R'—COO⁻ (Xa'), ⁻OOC—R⁵—COO⁻ (Xb') and R'—SO₃⁻ (Xc'), where R' and $R^5$ are each as defined above.

When, thus, the amino-containing organosilicon compounds are reacted with, for example, acetic acid, the organosilicon compounds according to the present invention will contain the acetate anions corresponding to the protonated nitrogen atoms.

The acids are preferably used in amounts of from 0.1 to 2.0 gram equivalents and more preferably from 0.5 to 1.5 gram equivalents, each numerical value being based on the amine nitrogen of the amino-containing organosilicon compounds, the amount of acid being determined in such a way that, per molecule, there is obtained at least one moiety of two protonated nitrogen atoms joined together through at least three carbon atoms.

When, thus, 1 kg of the amino-containing organosilicon compounds contains 14 g of basic nitrogen, it is for example preferable to use from 6 to 120 g of acetic acid and more preferable to use from 30 to 90 g of acetic acid. The use of from 6 to 60 g of acetic acid leads in this example to a partial protonation, i.e. not all the basic nitrogen atoms of the amino-containing organosilicon compounds are protonated. The use of 60 g of acetic acid or more provides fully protonated products, the excess acid serving to regulate the pH of the inventive ammonio-containing organosilicon compounds. The pH of the inventive organosilicon compounds can be lowered still further by adding even more acid. Mixtures of this type exhibit the characteristics of buffered systems.

It is preferable for all the basic nitrogen atoms in the inventive organosilicon compounds to be protonated, including any nitrogen atoms in the $R^3$ radicals, so that there are obtained as (a) structural unit Y of the formula (I) preferably those of the formula

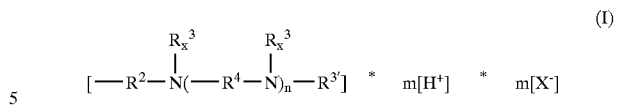

(I)

or, written differently,

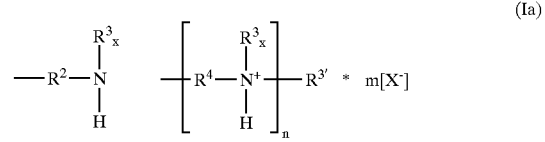

(Ia)

and, as optionally included (d) structural unit Y' of the formula (I') preferably those of the formula

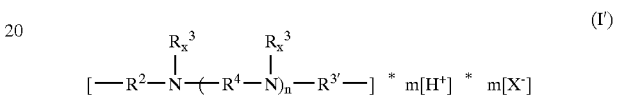

(I')

or, written differently,

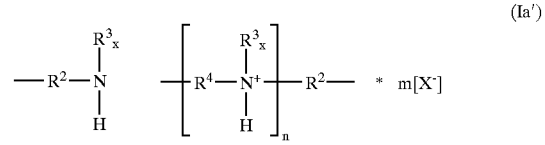

(Ia')

where m is equal to the sum formed from n+1 and the total number of any basic nitrogen atoms in the $R^3$ radicals, [i.e. at most m=n+1+(n+1)Σ(N atoms in $R^3$)]

$R^2$, $R^3$, $R^{3'}$, $R^4$ and $X^-$ are each as defined above, with the proviso that any basic nitrogen atoms present in $R^3$ are protonated.

The aqueous compositions according to the present invention contain organosilicon compound in an amount which is preferably in the range from 2 to 60% by weight and more preferably in the range from 2 to 20% by weight.

The aqueous compositions according to the present invention can be used in fields where ammoniosiloxanes have hitherto been used, chiefly as softeners for substrates such as fibers, textiles, hair; ie polymer-based natural or synthetic substrates.

The aqueous compositions according to the present invention may be stabilized by including (4) water-miscible solvents, such as isopropanol, diethylene glycol monomethyl ether, diethylene glycol monobutyl ether, dipropylene glycol or dipropylene glycol monomethyl ether.

These solvents can be added before or after the addition of acids. But it is preferable to add such solvents before any dilution with water.

If desired, it is also possible to use (5) emulsifiers to prepare the aqueous compositions, in which case nonionic emulsifiers are preferred.

The aqueous compositions according to the present invention have the advantage that the inventive ammonio-containing organosilicon compounds are preferentially soluble or self-dispersing in water and contain a lower level of basic nitrogen than previous organosilicon compounds. This holds especially in comparison with organosilicon compounds which contain amino or ammonium groups in which two nitrogen atoms are exclusively spaced apart by one or two carbon atoms.

The present invention further provides a process for impregnating organic fibers with the aqueous compositions according to the present invention.

The inventive process for impregnating organic fibers can be applied to any organic fiber in the form of filaments, yarns, webs, mats, strands, woven, loop-formingly knitted or loop-drawingly knitted textiles that have hitherto been impregnable with organosilicon compounds. Examples of fibers which are impregnable are fibers composed of keratin, especially wool, copolymers of vinyl acetate, cotton, rayon, hemp, natural silk, polypropylene, polyethylene, polyester, polyurethane, polyamide, cellulose and blends of at least two thereof. As is evident from the foregoing enumeration, the fibers can be of natural or synthetic origin. The textiles can be present in the form of fabric webs or garments or parts of garments.

Application to the fibers to be impregnated can be effected in any of the extensively described methods useful for impregnating fibers, for example by dipping, coating, casting, spraying, including spraying from an aerosol pack, rolling, padding or printing.

The aqueous compositions according to the present invention can further also be used in formulations such as creams, shaving foams, shampoos, washing lotions, soaps, deodorants or hairsprays.

A further emphasis is on the use for treating mineral materials, specifically for hydrophobicizing surfaces. Preference is here given to silicatic surfaces, to which the organosilicon compounds according to the present invention exhibit particularly good adhesion. The present invention accordingly provides a process for impregnating silicatic surfaces, especially glass, ceramics and natural rock, with the aqueous compositions according to the present invention.

The aqueous compositions according to the present invention can further be used for impregnating sheetlike organic plastics, such as vinyl acetate, polypropylene, polyethylene, polyester, polyurethane, polyamide and polycarbonate. The present invention accordingly provides a process for impregnating sheetlike organic plastics with the aqueous compositions according to the present invention.

EXAMPLE 1

197.8 g of an $\alpha,\omega$-bis(glycidyloxypropyl) polydimethylsiloxane having the average chain length Si-51 are mixed with 7.64 g of bis(3-aminopropyl)amine, 206 g of diethylene glycol monobutyl ether and 5.8 g of isopropanol. The thinly viscous mixture at 23 mm$^2$/s (25° C.) is heated to 130° C., whereupon the viscosity increases dramatically to a final value of 10 100 mm$^2$/s (25° C.) after 60 minutes. After cooling to 95° C., 11.5 g of acetic acid are stirred in. The solution contains 0.41 equ. of amine nitrogen per kg in protonated form (corresponds to 0.57% by weight of protonated amine nitrogen).

30 g of this solution are diluted with 70 g of water and spontaneously forms a pH-neutral, clear, aqueous formulation which is further thinnable in any desired proportion.

EXAMPLE 2

250.0 g of the epoxysiloxane of example 1 are mixed with 10.66 g of 1,6-diaminohexane, 260.0 g of diethylene glycol monobutyl ether and 7.5 g of isopropanol. After 2 hours at 130° C. the reaction mixture reaches a viscosity of 730 mm$^2$/s (25° C.). As it cools, 12.1 g of acetic acid are metered in. The solution then contains, per g, 0.35 meq. of protonated amine nitrogen (corresponds to 0.49% by weight of protonated amine nitrogen) and a pH of about 7.5. Further mixing with 2.3 times the amount of water provides a clear aqueous formulation.

EXAMPLE 3

255.0 g of the epoxysiloxane of example 1 are mixed with 12.77 g of dimethylaminopropylamine and 7.5 g of isopropanol and heated to 120° C. without further solvent. After a total of 6 hours, the viscosity has risen only to about 6 times the value (356 mm$^2$/s at 25° C.). The $^1$H NMR spectrum of this sample shows an epoxy group conversion of more than 99% of the amount used. The reaction product is freed of volatiles at 120° C. under reduced pressure to leave a clear oil having a viscosity of 620 mm$^2$/s at 25° C.

30 g of the basic aminosiloxane copolymer are mixed with 1.4 g of acetic acid and 30 g of diethylene glycol monobutyl ether and diluted with water to a total weight of 200 g. The neutral aqueous formulation contains, per kg, 106 meq. of protonated amine nitrogen (corresponds to 0.15% by weight of protonated amine nitrogen). It does not become cloudy on further dilution.

EXAMPLE 4

A 250 ml three-neck flask equipped with stirrer, reflux condenser and thermometer is charged with 100.0 g of a polydimethylsiloxane having trimethylsilyl end groups and glycidyl ether propyl side groups and having a viscosity of 1 420 mm$^2$/s at 25° C. and an epoxy content of 0.307 mmol/g, 6.1 g of 3,3-iminobis(N,N-dimethylpropylamine) and 15.9 g of 1-butanol. The contents are refluxed at about 135° C. for 6 hours with stirring. The slightly cloudy, weakly yellowish solution is heated out in a rotary evaporator at 150° C. under a full vacuum and subsequently filtered. The product obtained has an amine number of 0.91 mmol/g (corresponds to 1.27% by weight of amine nitrogen) and is weakly yellow and clear.

15.0 g of this polymer are dissolved in the same amount of diethylene glycol monobutyl ether and are protonated with 0.90 g of acetic acid. This mixture is diluted with water to 100 g by vigorous stirring. The aqueous solution obtained is clear and further dilutable without precipitation.

EXAMPLE 5

54 g of a hydrolysate of 3-aminopropyl-3-aminopropylmethyldimethoxysilane are dissolved with 1090 g of a commercially available silicone oil having trimethylsiloxane end groups and a viscosity of 1000 mm$^2$/s at 25° C. using 0.35 g of KOH and equilibrated in 0.9 g of methanol at 135° C. After 5 hours, the mixture is at equilibrium and the basic catalyst is neutralized with 0.45 g of acetic acid. Removal of the volatile siloxane cycles at 120° C. under reduced pressure leaves 996 g of an aminosiloxane having H$_2$N(CH$_2$)$_3$NH(CH$_2$)$_3$ groups.

30 g of this oil are dissolved in the same amount of diethylene glycol monobutyl ether and protonated with 1.2 g of acetic acid; water is then added to 200 g. The aqueous formulation obtained is clear and contains, per kg, 90 meq. of protonated amine nitrogen (corresponds to 0.13% by weight of protonated amine nitrogen).

What is claimed is:

1. An aqueous composition containing (1) ammonio-containing organosilicon compounds which, per molecule, contain at least one moiety of the formula

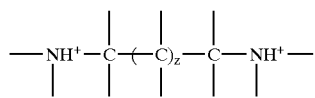

where z is an integer from 1 to 20,
(2) anions of an acid having a $pk_a$ greater than 0,
(3) water,
(4) optionally water-miscible solvents,
(5) optionally emulsifiers;
wherein the ammonio-containing organosilicon compounds contain
(a') at least one siloxane unit of the formula

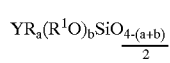 (IV)

where each R is the same or different and represents a monovalent optionally halogenated hydrocarbon radical having 1 to 18 carbon atoms per radical,
each $R^1$ is the same or different and represents a monovalent hydrocarbon radical having 1 to 8 carbon atoms per radical,
a is 0, 1, 2 or 3,
b is 0, 1, 2 or 3,
with the proviso that the sum of a+b is $\leq 2$,
Y is an organic radical of the formula

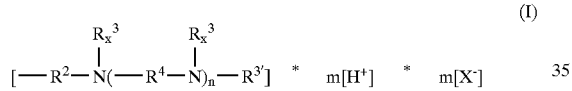 (I)

where $R^2$ is a divalent organic radical,
$R^3$ is a hydrogen atom or a monovalent hydrocarbon radical having 1 to 60 carbon atoms per radical which may be interrupted or substituted by one or more separate hetero atoms selected from the group consisting of nitrogen, oxygen, sulfur and halogen,
$R^{3'}$ has the meaning of $R^3$,
$R^4$ is a divalent hydrocarbon radical having 3 to 10 carbon atoms per radical,
n is 0 or an integer from 1 to 10,
m is an integer from 1 to the total number of nitrogen atoms in (I),
each x is the same or different and represents 1,
$X^-$ is an acid anion whose corresponding acid has a $pK_a$ value greater than 0, with the proviso that the structural unit of formula (I) contains at least one moiety of two protonated nitrogen atoms which are joined together by a hydrocarbon radical of at least three carbon atoms, and
(b) at least one siloxane unit of the formula

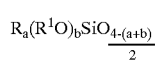 (II)

where R, $R^1$, a and b are each as defined above, and with the proviso that the sum of a+b is $\leq 3$;
and wherein the ammonio-containing organosilicon compounds contain (d') at least one bridging unit of the formula

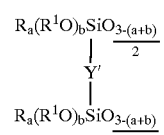 (V)

where R, $R^1$, a and b are each as defined above, with the proviso that the sum of a+b is $\leq 2$,
Y' is an organic radical of the formula

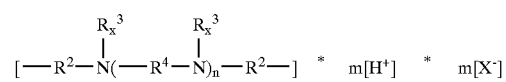 (I')

where $R^2$, $R^3$, $R^4$, n, m, x and $X^-$ are each as defined above, with the proviso that the structural unit of the formula (I') contains at least one moiety of two protonated nitrogen atoms which are joined together by a hydrocarbon radical of at least three carbon atoms.

2. An aqueous composition containing
(1) ammonio-containing organosilicon compounds which, per molecule, contain at least one moiety of the formula

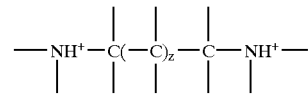

where z is an integer from 1 to 20,
(2) anions of an acid having a $pk_a$ greater than 0,
(3) water,
(4) optionally water-miscible solvents,
(5) optionally emulsifiers;
wherein the ammonio-containing organosilicon compounds contain
(a') at least one siloxane unit of the general formula

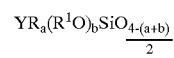 (IV)

where each R is the same or different and represents a monovalent optionally halogenated hydrocarbon radical having 1 to 18 carbon atoms per radical, each $R^1$ is the same or different and represents a monovalent hydrocarbon radical having 1 to 8 carbon atoms per radical,
a is 0, 1, 2 or 3,
b is 0, 1, 2 or 3,
with the proviso that the sum of a+b is $\leq 2$,
Y is an organic radical of the formula

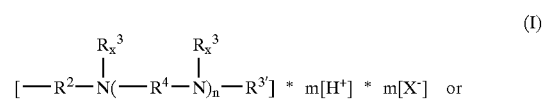 (I)

-continued

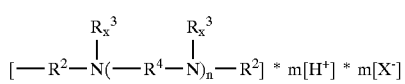
(I')

where $R^2$ is a divalent organic radical, $R^3$ is a hydrogen atom or a monovalent hydrocarbon radical having 1 to 60 carbon atoms per radical which may be interrupted or substituted by one or more separate hetero atoms selected from the group consisting of nitrogen, oxygen, sulfur and halogen, $R^{3'}$ has the meaning of $R^3$, $R^4$ is a divalent hydrocarbon radical having 3 to 10 carbon atoms per radical, n is 0 or an integer from 1 to 10, m is an integer from 1 to the total number of nitrogen atoms in (I), each x is the same or different and represents 1, $X^-$ is an acid anion whose corresponding acid has a $pK_a$ value greater than 0, with the proviso that the structural unit of formula (I) contains at least one moiety of two protonated nitrogen atoms which are joined together by a hydrocarbon radical of at least three carbon atoms, and (b) at least one siloxane unit of the general formula

(II)

where R, $R^1$, a and b are each as defined above, and with the proviso that the sum of a+b is ≦3;

and wherein at least one $R^2$ is an organic radical selected from the group consisting of

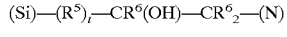
(VI), and

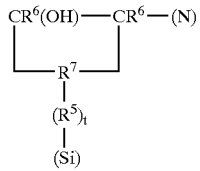
(VII)

where (Si)— is the bond to the silicon atom of the siloxane unit of the formula (IV) or a radical (V)

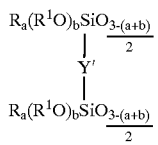
(V)

and —(N) is the bond to the nitrogen atom of the radical Y or Y' of the formula (I) or (I'), $R^5$ is a divalent hydrocarbon radical having 1 to 10 carbon atoms per radical which may be substituted by an ether oxygen atom, $R^6$ is a hydrogen atom or a monovalent hydrocarbon radical having 1 to 10 carbon atoms per radical which may be substituted by an ether oxygen atom, $R^7$ is a trivalent hydrocarbon radical having 3 to 12 carbon atoms per radical and t is 0 or 1.

3. A process for impregnating a siliceous surface, comprising contacting said surface with an aqueous composition comprising at least one (1) ammonio-containing organosilicon compounds which, per molecule, contain at least one moiety of the formula

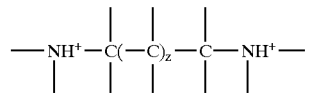

where z is an integer from 1 to 20, (2) anions of an acid having a $pk_a$ greater than 0, (3) water, (4) optionally water-miscible solvents, and (5) optionally emulsifiers.

4. An aqueous composition containing (1) ammonio-containing organosilicon compounds which, per molecule, contain at least one moiety of the formula

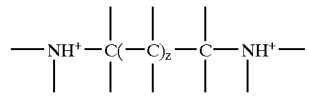

where z is an integer from 1 to 20, (2) anions of an acid having a $pk_a$ greater than 0, (3) water, (4) optionally water-miscible solvents, and (5) optionally emulsifiers, and wherein said moiety is bonded minimally, at least one nitrogen atom to an organopolysiloxane, through a linking group comprising

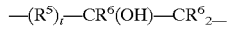

wherein $R^5$ is a divalent hydrocarbon radical having 1 to 10 carbon atoms per radical which may be substituted by an ether oxygen atom, $R^6$ is a hydrogen atom or a monovalent hydrocarbon radical having 1 to 10 carbon atoms per radical which may be substituted by an ether oxygen atom, and t is 0 or 1.

5. The aqueous composition of claim 4, wherein said ammonio-containing organosilicon compounds are prepared by reacting an epoxy-containing organosilicon compound containing units of the formula

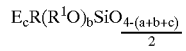

where R is the same or different and represents a monovalent optionally halogenated hydrocarbon radical having 1 to 18 carbon atoms per radical, each $R^1$ is the same or different and represents a monovalent hydrocarbon radical having 1 to 8 carbon atoms per radical, a is 0, 1, 2 or 3,
b is 0, 1, 2 or 3, and
E is an Si—C bound epoxy group, and
c is 0 or 1,
with
a polyamine of the formula

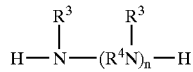

wherein $R^3$ is a hydrogen atom or a monovalent hydrocarbon radical having 1 to 60 carbon atoms per adical which may be interrupted or substituted by one or more separate hetero atoms selected from the group consisting of nitrogen, oxygen, sulfur and halogen, and $R^4$ is a divalent hydrocarbon radical having 3 to 10 carbon atoms per radical, n is 0 or an integer from 1 to 10, and protonating the reaction product by addition of an acid having a pKa>0.

6. An aqueous composition comprising:
(1) an ammonio-containing organosilicon compound which, per molecule, contain at least one moiety of the formula

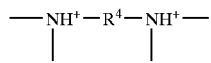

wherein $R^4$ is a $C_{3-20}$ hydrocarbon, (2) anions of an acid having a $pk_a$ greater than 0,
(3) water,
(4) optionally water-miscible solvents, and
(5) optionally emulsifiers, wherein said ammonio-containing organopolysiloxane comprises two organopolysiloxane moieties each bound through a divalent linking group to different nitrogen atoms of a species of the formula

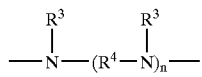

or its protonated equivalent, where $R^3$ is a hydrogen atom or a monovalent hydrocarbon radical having 1 to 60 carbon atoms per radical which may be interrupted or substituted by one or more separate hetero atoms selected from the group consisting of nitrogen, oxygen, sulfur and halogen $R^4$ is a divalent hydrocarbon radical having 1 to 10 carbon atoms per radical, and n is an integer from 1 to 10.

* * * * *

UNITED STATES PATENT AND TRADEMARK OFFICE
CERTIFICATE OF CORRECTION

PATENT NO. : 6,878,770 B2
DATED : April 12, 2005
INVENTOR(S) : Christian Herzig et al.

It is certified that error appears in the above-identified patent and that said Letters Patent is hereby corrected as shown below:

Column 21,
Line 25, after "formula" insert

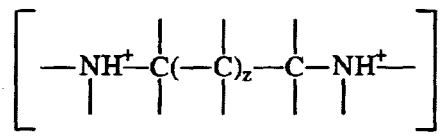

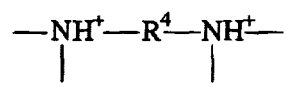

Signed and Sealed this

Fourth Day of October, 2005

JON W. DUDAS
*Director of the United States Patent and Trademark Office*